United States Patent [19]

McMillan et al.

[11] Patent Number: 5,170,193

[45] Date of Patent: Dec. 8, 1992

[54] APPARATUS AND METHOD OF IDENTIFYING SIGNALS IN BIOLOGICAL TISSUES

[75] Inventors: Charles F. McMillan, Livermore; H. Alfred Sklar, San Francisco, both of Calif.

[73] Assignee: Phoenix Laser Systems, Inc., San Francisco, Calif.

[21] Appl. No.: 656,722

[22] Filed: Feb. 19, 1991

Related U.S. Application Data

[63] Continuation-in-part of Ser. No. 456,109, Dec. 22, 1989, Pat. No. 5,054,907.

[51] Int. Cl.[5] ............................................. A61B 3/10
[52] U.S. Cl. ..................................... 351/212; 351/247
[58] Field of Search ................. 351/212, 247; 356/376

[56] References Cited

U.S. PATENT DOCUMENTS 4,312,574 1/1982 Wilms .................................. 351/212
4,878,750 11/1989 Sekiguchi ........................... 351/212

Primary Examiner—Rodney B. Bovernick
Attorney, Agent, or Firm—Thomas M. Freiburger

[57] ABSTRACT

The present invention describes a technique and apparatus for finding spots in an image with substantial noise making it difficult to identify without specialized noise suppression algorithms. In the context of determining corneal shape, as an example of the technique, the reflections of point light sources in or on the cornea have long played a diagnostic role. The image analysis technique described applies the tools of mathematical morphology and prior information about the shape of illumination patterns to remove noise and isolate the points of interest for further mathematical analysis. The output from the technique is a set of pairs matching the detected points in the image with the known location of the illumination.

17 Claims, 7 Drawing Sheets

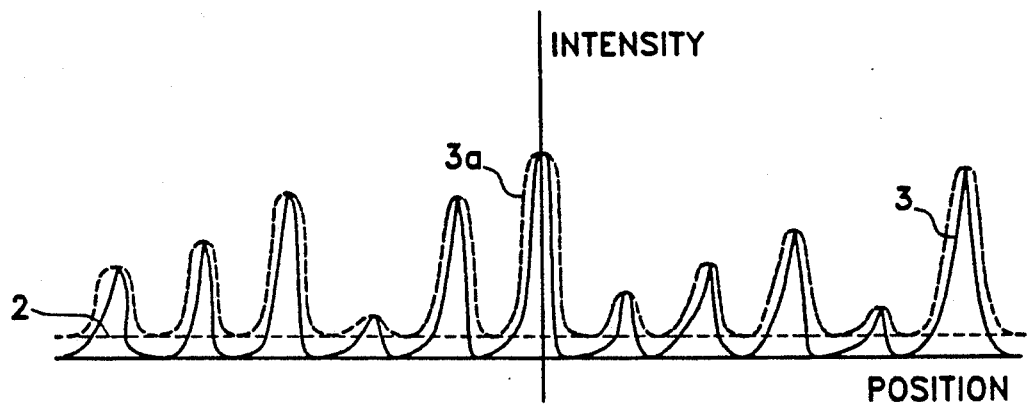
Fig. 3a
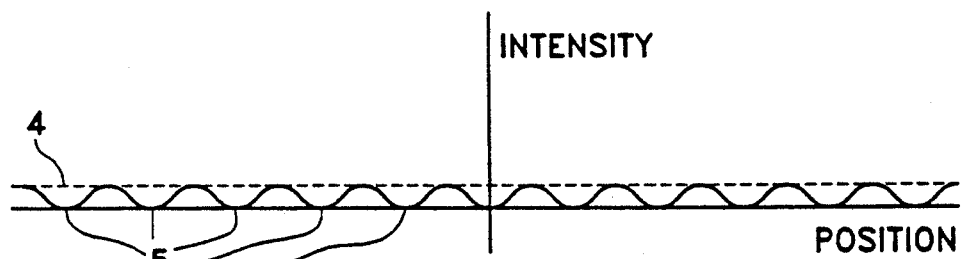
Fig. 3b
Fig. 4

APPARATUS AND METHOD OF IDENTIFYING SIGNALS IN BIOLOGICAL TISSUES

REFERENCE TO RELATED APPLICATION

This application is a continuation-in-part of copending U.S. application Ser. No. 456,109, filed Dec. 22, 1989, now U.S. Pat. No. 5,054,907.

BACKGROUND OF THE INVENTION

The invention relates generally to optics, and more particularly to an imaging system wherein noise filtering techniques are employed to increase the signal to noise ratio used in analyzing the image.

In many biological systems, a method of preference for identifying the location, shape, or other characteristics of a tissue is to shine light or some other form of radiation onto the tissue and observe either how the light is reflected, absorbed, refracted, or scattered by the tissue. Inherent to observing the radiative effect on said tissue is the ability to detect a signal emanating from the tissue as a consequence of disturbing the tissue in some designated fashion. Many biological structures, however, are very sensitive to light or other forms of radiation thus limiting the threshold of signal that can be used to generate nondamaging responses. Even more troublesome is that many biological tissues have weak reflectivity or weak scattering properties so that the pertinent signal resulting from the disturbance is difficult to detect. This presents the observer with the compound problem of having to detect weak signals and low signal to noise ratios.

This is illustrated herein by discussion of the anterior surface of the eye's cornea known as the epithelium, although this discussion applies to any reflecting surface within the eye. When trying to define the surface topography of the epithelium, it is often desirable to shine point sources of light onto the epithelium from a precisely established location and to measure very accurately on a detector the location of the reflected image from said point source. However, point sources are a distribution of energy about some given location and said distribution is not generally constant or uniform from source to source. Since these energy distributions are reflected from unspecified surfaces at unpredetermined angles of incidence and with varying reflectivity and scattering, the identification of the reflected images of the point sources can be a difficult problem, especially when low illumination levels are desired.

The accuracy of the technique used by Sklar et al. to measure the surface profile of the cornea (U.S. patent application Ser. No. 456,109, now U.S. Pat. No. 5,054,907) hinges on the ability of the apparatus to measure the location of the rays from point sources in front of the eye as they are reflected from the cornea. As described by Sklar et al., the reflected rays are detected by an imaging device such as a CCD camera and digitized using a frame grabber card in a computer. Other perimeter devices used to measure eye features also rely upon accurately measuring the response of the eye to shining light onto the eye. In general, the observed reflections of these spots of light are embedded within a nonuniform background which may be very close to the noise floor level for contrast selectivity or threshold filtering because of poor light source edge definition and because of low reflectivity from the corneal epithelium.

The process of separating the spots of reflected signal from the background light and locating the peak or center of the signal presents a challenging image processing problem which can be crucial to the success of the entire surface profiling procedure. The apparatus and methods for obtaining the accurate location of such signals are the subject matter of this invention. These techniques are by no means restricted to ophthalmic applications, or even biological systems. These types of techniques have been in use in military applications where targets are at times difficult to differentiate from the background field and where filtering techniques such as thresholding and fast Fourier transform filtering prove unsuccessful. In medicine and, in particular, in surgery, computers have only recently begun to be incorporated as part of surgical devices. Since the techniques that are the subject of this invention require substantial calculation, these techniques have only recently become possible in a surgical environment.

As described further below, the apparatus and methods that are the subject of this invention use nonlinear filtering techniques of mathematical morphology many of which originated with the pioneering work of J. Von Neumann for developing automated devices to analyze images by comparing a given pixel of the image with its immediate neighbors. Many of these nonlinear filtering techniques are described by Serra (*Image Analysis and Mathematical Morphology*, Jean Serra, Academic Press 1982) and borrow from the fields of algebraic topology, harmonic analysis, stochastic processes, integral geometry, and others. We apply these nonlinear filtering techniques of mathematical morphology to the problem of isolating and identifying the centers of reflected point light sources. In the case of the invention described by Sklar et al. (U.S. patent application Ser. No. 456,109, now U.S. Pat. No. 5,054,907) the purpose for identifying said reflected light sources, herein after referred as "points", is to present the data to a surface profiling algorithm to determine the topography of the corneal surface. In other uses of the present invention not only different structures are to be described, but different types of image sources and scattering as well as absorptions, reflections, or refractions can be considered.

The problem of identifying the location of the centers of the points is addressed in three stages. First, the points must be isolated. Then we must look for and recognize symmetry in the pattern of points. And finally, we have rejection of noise pulses which have eluded previous elimination criteria.

SUMMARY OF THE INVENTION

In accordance with the present invention, an apparatus and method for identifying the location of the centers of signals with poor signal to noise ratios and poor background differentiation are described. The method calls for first isolating the signal "points", recognizing the symmetries in the point patterns, and suppressing noise signals which have eluded previous elimination.

Since the recorded image background is frequently nonuniform due to scattering from the instrument, dust particles in the air, or even from the target, the first step in isolating the point signals is subtraction of the background. This is accomplished by subtracting a morphological gray-scale opening of the image using a circular kernel, which corresponds to an erosion followed by a dilation, from the original picture. The terms "erosion", "dilation", "opening", "closing", "morphological operations", "circular kernel", "hit or miss topology" and so forth are intended in their algebraic sense as defined by J. Serra as cited above. For example, given two finite sequences $G_1, \ldots, G_i, \ldots, G_m$ of open sets and $K_1, \ldots K_h, \ldots, K_n$ of compact sets in a real space of N dimensions, the class of all closed sets which hit every $G_i$ and miss every $K_h$ defines an open neighborhood in the space F of all closed sets in a real N dimensional space.

In the present invention, the size of the kernel is chosen so as to remove all features smaller than the approximate size of the dots from the image. The size of the dots is a known quantity since it is related to the illumination source. In the embodiment of the invention described below this corresponds to using a circular kernel of radius 3 pixels since the point sources are being magnified by the internal optics of the system to reflections which appear of that size to the detector observing the reflections. This first level of filtering of the original image, hereinafter referred to as $I_0$, shown in FIG. 1, leaves the resultant image, hereinafter referred to as $I_1$, shown in FIG. 2, with a level background and tends to equalize the maximum light intensities observed from the dots by reducing the more intense spots proportionately more than the fainter spots.

The next step in the process of isolating the points is to locate the peak intensities of the spots. This operation involves a combination of dilation with thresholding. A copy of the result of the first level of filtering described above, $I_1$, is stored in computer memory while a second image, $I_2$, is generated by applying a threshold transformation to $I_1$. As a consequence of this threshold filtering transformation, all pixels that composed $I_1$ which were below the threshold value are set to the threshold value while those above the threshold are left unchanged.

The threshold value is determined experimentally and is determined according to the types of light sources, optical elements, and targets to be identified. The threshold value is chosen to be low enough to be below the expected intensity level of the spots originating from the source light pattern, but above most of the observed random noise emanating from the floor. A dilation is then applied to the image $I_2$ once again using a circular kernel. The effect of this second filtering operation is to leave the maximum intensity of each spot unchanged and at the same location while spreading said maximum value of the spot around the peak location outwards to the full extent of the radius of the circular kernel. These peak values are determined by subtracting $I_1$ from $I_2$ and looking for areas in the resulting image whose intensities are identically zero. These areas of zero intensity correspond to the regions in image $I_2$ that were above threshold and represented local intensity maxima within the region determined by the radius kernel since they were unchanged between the original image $I_0$ and the dilated image. The effect of these operations is shown in FIGS. 3 and 4.

The choice of kernel radius for the dilation kernel must be based on the separation distance between adjacent spots in the light source which gave rise to $I_0$ and the anticipated smoothness of each of the intensity peaks observed. In practice, an illumination mask or a pattern of light sources is used with a given separation distance between the originating light spots. In ophthalmic applications where you are investigating the shape of the cornea, the distance between light spots is selected to correspond to the desired resolution as projected through the optical instrument of the apparatus onto the 12 millimeters which defines the diameter of the cornea taking into account the magnification of the apparatus as seen by the detector. In practice, the kernel radius should not exceed approximately half the average separation between intensity peaks. We say average because in general a uniform distribution of the peaks is neither required or optimally desirable.

For reasons of computational speed, it is preferable to make the kernel radius as small as possible. One of the limitations to reducing the kernel radius is that if the peaks are too jagged, the difference operation described above will reveal a variety of local minima rather than a single point at the peak of the spot whenever the smaller peaks are separated by more than the kernel radius. This proliferation of intensity peaks leads to confusion and degradation of the result. Fortunately, we can test for adequate choices for the kernel radius during experimental phases of setting up the apparatus for a given application in order to avoid the problem of proliferating peaks. Alternatively, the apparatus is set up to allow for modification of the kernel radius whenever the resulting image definition is insufficient because of the detection of excessive number of intensity peaks. For corneal topography applications we use a kernel of radius 5 pixels.

The resulting image $I_2$ described above as a result of the morphological transformations is to produce a list of points in $I_2$ made up primarily of the light rays originating in $I_0$ and reflected from the surface of the cornea. It is anticipated that $I_2$ will also contain some spurious noise spikes.

The next step in the process is to use knowledge of light source distribution symmetries to further suppress noise in $I_2$. The operation now is to find the center of an approximately symmetrical pattern so that it can be used to segregate a number of lines that pass through this center into separate groups. We say approximately symmetrical patterns for two principal reasons. First, the optics of the system and the reflecting surface itself will introduce some level of pattern distortion into $I_2$. Second, there is no requirement that we restrict discussion to only one pattern or even one type of pattern. Thus, to simplify the analysis a sorting into distinct pattern groups is desirable. An example of how these points might be distributed is shown in FIG. 5a.

In one embodiment of the present invention, the ophthalmic application described herein, a star shaped distribution of light sources being projected through the objective lens of a surgical workstation (Sklar et al, U.S. patent application Ser. Nos. 475,657 and 456,109, now U.S. Pat. No. 5,054,907) was selected as the desired mask in order to provide high definition of corneal curvatures in the neighborhood of the visual axis of the eye as well as a measure of angular asymmetry.

Even though the light source or input template used to produce the illumination pattern is symmetrical in this embodiment of the invention, the output pattern as observed by the detector is typically not symmetrical. Variations in illumination intensity which give rise to asymmetries can be caused by difference in fiber coupling the light source to the fiberoptic waveguides used to establish a pattern, or differential losses within the waveguide, or pinhole size variations is fabricating a mask for the illumination source. Such variations can lead to loss of detectable spots in the image $I_2$. Other mechanisms for spot loss can be ascribed to variations in reflectivity from the target being examined and even from image processing. The noise spots that have either been created through the image processing or which have survived the various filtering operations described above will not generally be distributed symmetrically. Even more important, the distribution of noise spots are unlikely to correspond to the preselected source symmetries even when distorted. This information is used in further suppressing noise spots.

The process for finding the center of the pattern begins by going through the pattern and assuming that each peak in the pattern is the center of the pattern. The assumption that each peak is the center of the pattern is then tested by examining the reflection of each other spot in the pattern about the supposed center and searching for existence of another spot close to the reflection. Namely, the vector from the assumed center to the test point is reversed. If there exists another point near the reflection, the given score scale value for that particular assumed center is increased. After sequentially going through this process of testing each peak for closest neighbors with every surviving spot in $I_2$, the peak with the highest score corresponds to the center. This process is illustrated in FIG. 5b.

This process of locating the center is calculationally time consuming. It is, however, very robust. It successfully locates the center of a given illumination pattern as reflected by the eye even when many spots are missing or with a multiplicity of extraneous noise spots. When dealing with the variety of ailments which are often encountered by ophthalmologists, keratoconus being one notable case, surface aberrations can frequently cause illumination spots to go astray. A robust system of detection which will allow an instrument to perform irrespective of such variation was one of the motivations in the design of the present invention. With the computational capacity available today with high performance dedicated computer boards using 80386 and 80486 based microprocessor with specialized mathematical coprocessor chips and vectored accelerator boards, the calculational time of the processes described herein which were formerly practicable on mainframe computers become accessible to commercial uses and surgical environments.

The template pattern 46 described in FIG. 9 and the pattern 82 in FIG. 11 of Sklar et al. (U.S. application Ser. No. 456,109) correspond to a sequence of light sources arranged along a number of intersecting straight lines. If we apply the above general discussion to these templates, the effort in finding the center of the pattern reduces to locating the intersection point for the straight line patterns as observed in image $I_2$. Once the center of the pattern is established, the approximately straight lines of spots radiating outward from this center in image $I_2$ are easily identified by collecting spots together that have approximately the same angle relative to the axis of the line based upon the arctangent value at the given spot.

The grouping of spots into independent straight lines can be based upon the a priori knowledge of the number of such straight lines which composed the initial illumination pattern as described in FIG. 9 and 11 noted above. Thus, the correct number of angular bins can be chosen for the collection system as well as reasonable values for the boundaries of the bins. In other words, we are using knowledge of the shape of the illumination pattern in order to improve noise suppression in a system with poor signal to noise ratios.

In our illustrative example, we use eight straight lines of illumination source points passing through the center shown in FIG. 6. We thus divide the spots observed in $I_2$ into eight separate bins using angles midway between each known line as the bin boundaries. So far, we have used the knowledge that the illumination light sources have been arranged along discrete and distinct patterns and we have used the existence of such patterns to locate the center of the pattern and to sort the observed spots into distinct bins or subpatterns. We now proceed to use knowledge of the original shape of the distinct illumination pattern to further suppress noise.

The final noise rejection operation in the system is based upon a priori knowledge of the configuration of the illumination system. In the example noted above concerning topographical mappings of the eye's cornea, the subpatterns described in FIGS. 9 and 11 correspond to straight lines intersecting at some center point. The angles of each line with respect to one another are predetermined during fabrication of the illumination masks. Using this information, the spots in image $I_2$ were segregated into individual groups or bins. Each grouping of points in a bin can then be approximately rotated to the horizontal axis by making use of the knowledge of the angular relation between each line in the illumination mask.

Any point within the group lying more than a preselected number of pixels off the horizontal axis following the rotation is identified as a noise pixel and deleted from the image. This operation is shown in FIG. 6. In practice, we have found that a discrimination value of 5 pixels is adequate for the task of noise suppression. After elimination of such noise pixels, the subpatterns can be counterrotated to its corresponding alignment to form image $I_3$. In general, there is no requirement that the subpatterns correspond to straight lines or that the superposition transformation be isometric. It is important however that the patterns be selected so as to permit superposition transformations which are invertible.

Once the points that are well away from the true line have been eliminated, the resulting pattern $I_3$ is compared with a stored calibration pattern where the scales of the two patterns are matched by comparing the average spacing between points in each line subpattern. Points which do not have a mate in the calibration pattern are further ignored before proceeding to the profiling procedure. Examples of such profiling procedures are discussed in Sklar et al U.S. Pat. No. 5,054,907.

DESCRIPTION OF THE DRAWINGS

FIG. 3a shows a trace 3 of image $I_1$, a reasonable threshold value 2, and a trace 3a across the dilated threshold image. The difference between trace 3 and trace 3a is shown in FIG. 3b with trace 4 representing the threshold level and the points 5 representing the points at which the difference is identically zero indicating the local maxima of trace 3.

FIG. 4 shows the resulting image after the difference operation with the threshold set so that only the null points are visible.

DESCRIPTION OF PREFERRED EMBODIMENTS

Figure 7:
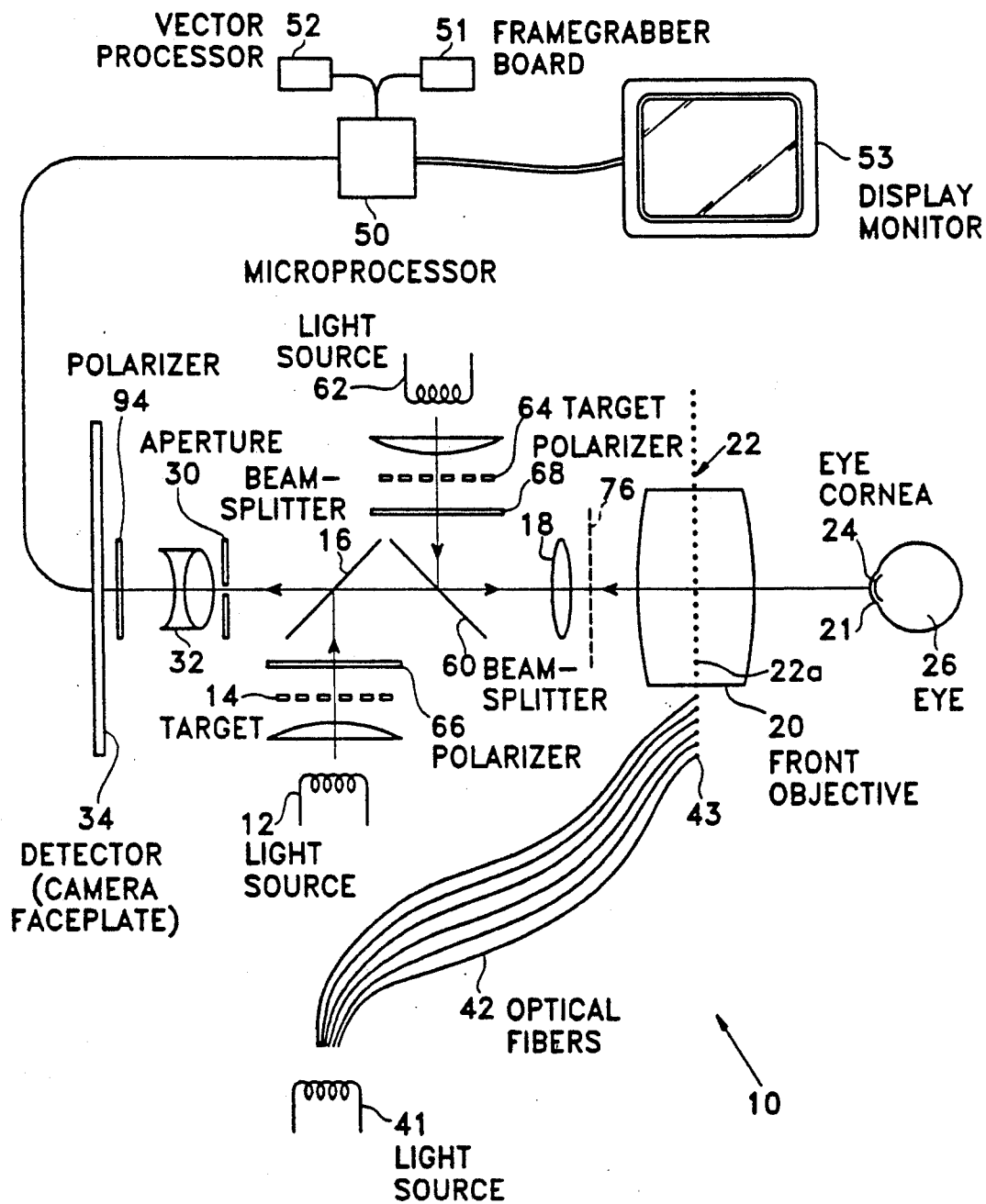
FIG. 7 shows an embodiment of an apparatus which illuminates the target and provides the optical means for detecting the signal and sending it the microprocessor means that initiates the noise suppression techniques discussed herein.

In the drawings, FIG. 7 shows in schematic representation an example of how an instrument would make use of the noise suppression features and methods of the present invention. It describes a system of optical elements in accordance with the invention for use in carrying out ophthalmic diagnosis and analysis similar to a device taught by Sklar et al. (U.S. patent application Ser. No. 456,109).

The system, generally identified by the reference number 110, includes an illuminator or light source 12, a pattern plate or disk 14 having a pattern of holes cut in the plate for producing a desired pattern of discrete light sources, a non-distorting beam splitter 16, a lens 18 which projects an image of target 14 onto an image plane at 22. This image plane 22 is close to or coincidental with the system of objective lens 20. The purpose of displacing the image at this location 22 is to have the objective lens 20 serve as a field lens, that is bending the rays of light 22a that form the image towards the patient's cornea 21.

As indicated in FIG. 7, the focused image 22 of the pattern is a real image, formed at some plane at or near the lens 20 and between the lens and the patient. The real image preferably is in the lens 20, but it can be very closely in front of the lens (i.e. a few millimeters in front) or behind the lens. The importance is that the focused image 22 lie along the optical path passing through the lens 20 which can give optimal definition along the visual axis of the cornea. In this real image, each point source of light 22a projects a cone of light towards the patient. Thus, each point source 22a in the real image makes an infinite number of specular reflections off the front surface of the cornea 24 of a patient's eye 26. In addition to the focused image 22, it may prove desirable to extend the range of coverage of a curved reflecting surface 21 by projecting a longer array of image points 22a than can be projected through the final lens 20.

Towards this end, a light source 41 illuminates a fiberoptic bundle 42 whose polished terminations 43 serve as additional image points to the image points 22a located within or directly in front of the final lens 20. The purpose of light points 43 is to increase the length of the image line 22 and thus provide more extensive peripheral definition of cornea 21 away from the visual axis of the eye. The position of light points 43 is adjusted so as to lie along the plane of pattern 22.

Alternatively, even for conventional perimeter devices that only utilize light sources as described by light points 43, the present invention provides a means for improving the detection of said light points 43 when poor signal to noise ratios are perceived by the detector 34. This enables weak light sources 12 and 62 to be utilized without sacrificing resolution, and thus minimize discomfort to the patient or light toxicity to the patients eye.

The F-number of the final lens 20 determines the maximum area of the cornea that can be measured. The objective lens serves as a field lens, and the patient's cornea must be at the focal length of the lens 20. A preferred method for assuring that the eye is located at the focal length of the lens 20 is discussed in Fountain et al. (U.S. patent application Ser. No. 655,919). This assures that the light reflected off the eye parallel to the optical axis of the instrument is then brought to a point behind the lens 20 at the focal distance of the lens 20. This enables the return light to be apertured down, to select only those rays which were paraxial off the eye. This enables the system to localize a detected point to a point on the cornea from which that ray is reflected. If the objective lens 20 were not situated to serve as a field lens, outermost points of light in the pattern would not reflect off the cornea. As a field lens, the lens 20 efficiently bends the outer points of light toward the eye.

It is preferred that the focal length of the lens be great enough to provide an unobstructed, comfortable distance from the instrument to the patient and adequate working room for the surgeon, for surgical applications.

FIG. 7 schematically indicates that the detector or camera plane 34 is connected to a microprocessor 50 which may contain a frame grabber board 51 which digitizes the images detected by detector 34 together with a vector processor 52 for speeding the calculations. The microprocessor may be connected to a display device, such as a CRT monitor 53 as indicated. Data gathered from the system as described is received by the microprocessor 50 and analyzed. As described below, each detected point is correlated with the location of the particular point in the source pattern from which it emanated. This information is then provided to an algorithm as described by Sklar et al. (U.S. patent application Ser. No. 456,109, now U.S. Pat. No.

5,054,907) for display as part of a user interface, for ophthalmic surgical procedures such as described by Sklar et al. (U.S. patent application Ser. No. 307,315 now U.S. Pat. No. 5,098,241 and Ser. No. 475,657) or for diagnostic verification of the eye's topography.

Figure 8:
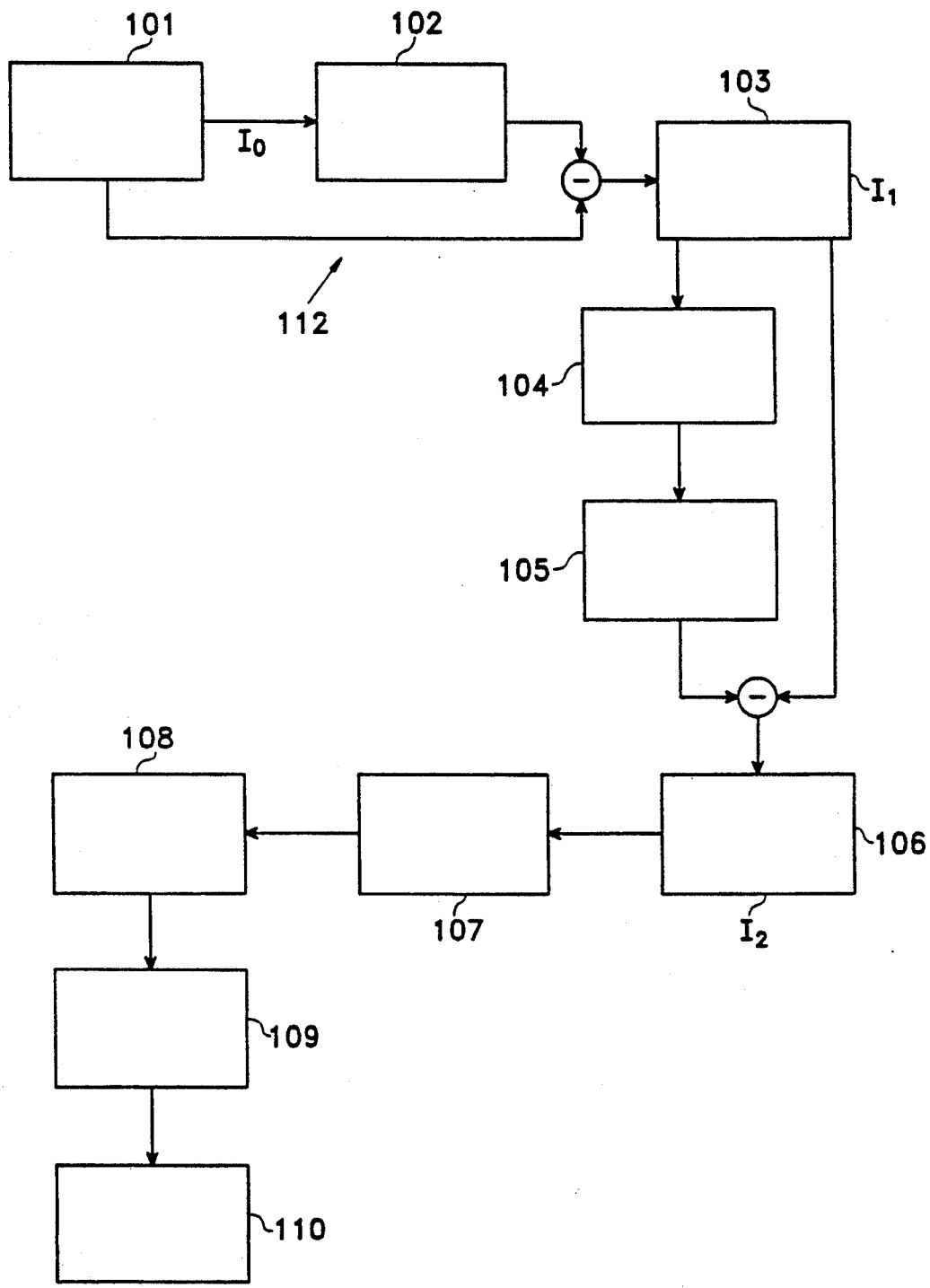
FIG. 8 is a schematic drawing of the information flow for the filtering techniques that are a part of the present invention. The frame grabber board 101 inputs the image $I_0$ to the image opening operation 102. We then develop at 103 the image of $I_0$ with the background removed. The thresholding operation 104 replaces all intensity values less than the threshold by the threshold value and is followed by the dilation operation 105. The pattern 106 selects the points that are identically zero representing the local maxima in $I_0$. The process of finding the center of the pattern 107 uses symmetry scoring. Next follows the process 108 of segregating the spots into lines based on the a priori information about the angles of the lines in the illumination source. The process 109 of rejecting the spots which are off the line after rotation then follows. The final step 10 denotes the process of matching the spots in the image lines to spots on the target lines. Non-matching spots are deleted.

FIG. 8 shows a chart of the flow of information and the multiple steps taken in filtering the noise from an image such as those contemplated in the present invention. The chart, discussed above, traces the various mathematical morphological transformations which are applied to the images generated in the particular case of the configuration shown in FIG. 7 which constitutes an application in the field of ophthalmology.

Figure 1A:
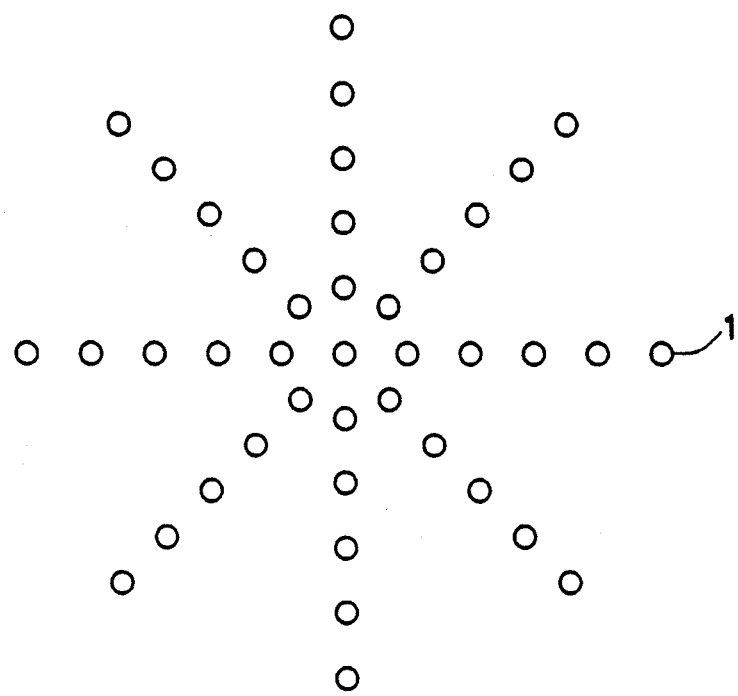
FIG. 1a shows the illumination pattern $I_0$ of the light reflected from the cornea or from the tear layer overlying the cornea as digitized by the frame grabber. A trace across the pattern at 1 shown in FIG. 1b illustrates the nonuniform peak heights and background.
Figure 1B:
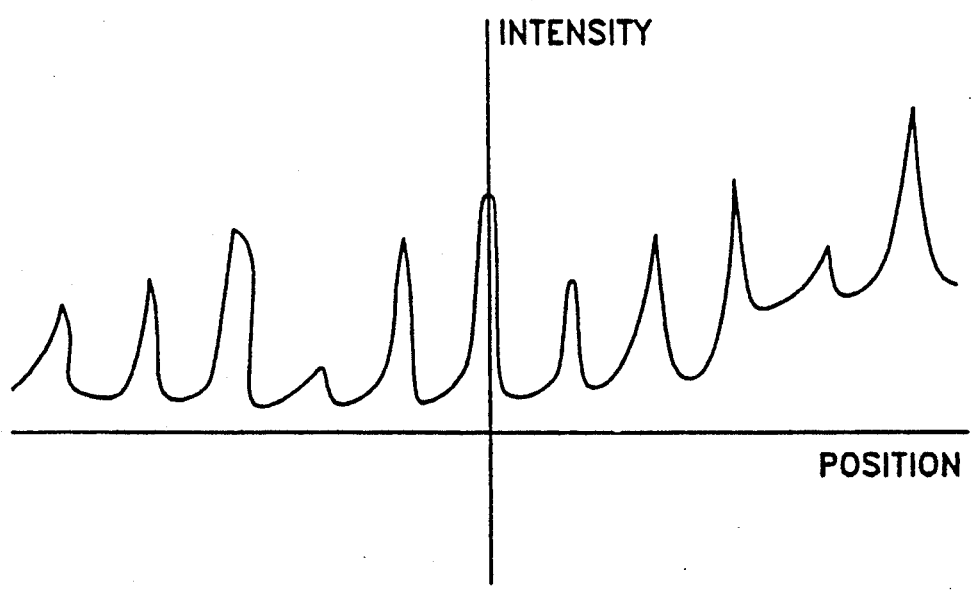

As explained above, FIG. 8 describes the flow of information from the frame grabber 101, noted as the frame grabber means 51 in FIG. 7, to the profiling system. The image from the frame grabber 101 is shown in FIG. 1a. It is formed by the light from the spots 22 in FIG. 7 reflecting from the cornea or the cornea's tear layer, passing through the aperture, and hitting the detector. A trace across this pattern along the line shown as 1 in FIG. 1a shows the intensity along the line as a function of position. The result is shown in FIG. 1b. The pattern in FIG. 1b is referred to as the image $I_0$.

Figure 2A:
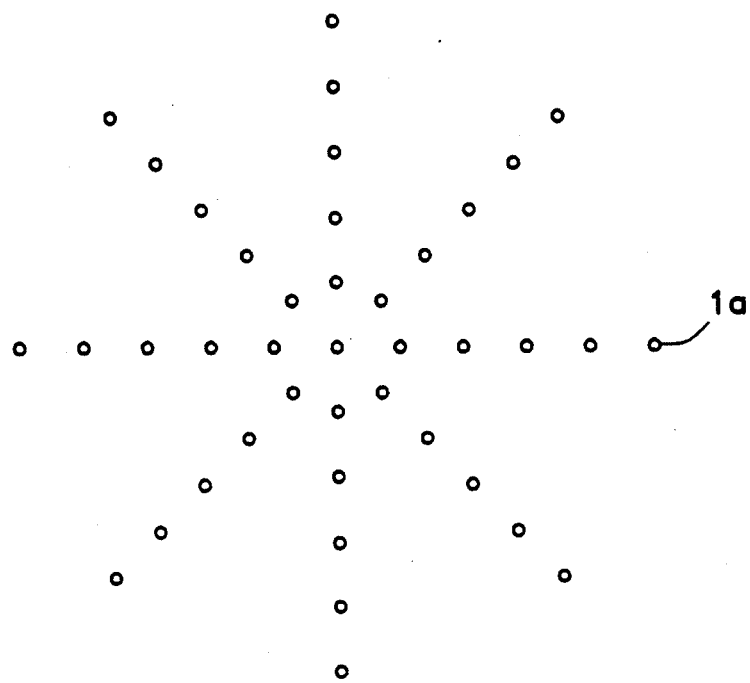
FIG. 2a shows the illumination pattern $I_1$ after the background has been subtracted.
Figure 2B:
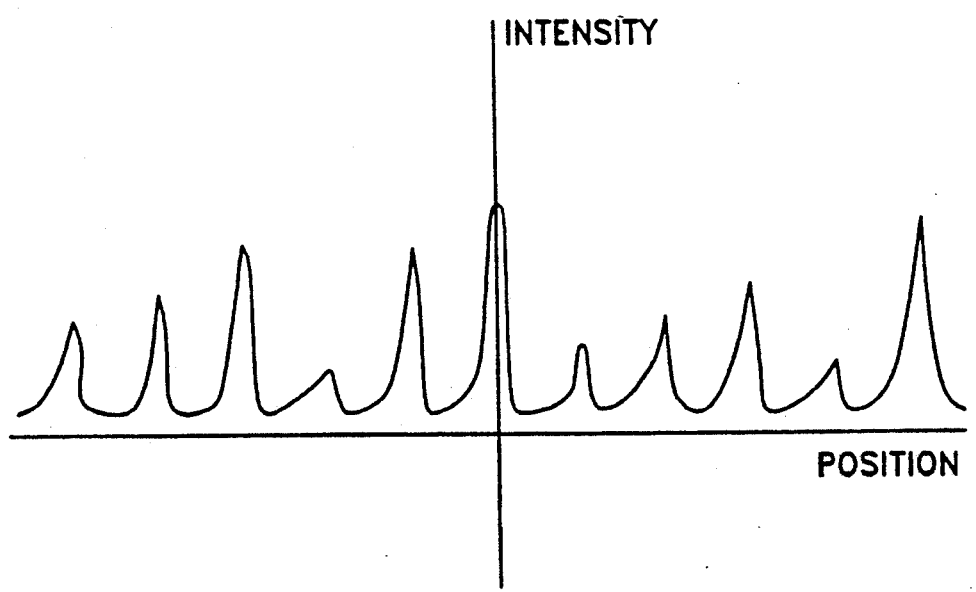
FIG. 2b shows a trace across the pattern illustrating the equalization of the background level.

A copy of $I_0$ is passed through the morphological opening operation using a circular kernel shown as 112 in FIG. 8. The difference between the original image Iand this opening is represented by 103 in FIG. 8. We refer to this image as $I_1$. The effect of the opening and the difference is to equalize the background level throughout the image, thus effectively removing the background from the resulting image shown in FIG. 2a with a trace across the pattern illustrating the equalization of the background level when compared with FIG. 1b.

While a copy of $I_1$ is maintained, the information is passed first through a thresholding operation in which all pixel values in the image less than the threshold value are set to the threshold value, represented schematically as 104 in FIG. 8, the output of which passes through a dilation operation 105 in FIG. 8. The effect of these operations is shown in FIG. 3a. In FIG. 3a, the line 3 shows a trace across $I_1$, and 2 represents a reasonable threshold level. Trace 3a shows what the trace looks like after both thresholding and dilating. The difference between $I_1$ and the thresholded and dilated image is noted in 106 of FIG. 8. This difference is referred to as image $I_2$ and is shown in FIG. 4. The places in $I_2$ that are identically zero represent the local maxima of $I_0$, which are the points sought by this technique. A trace across this pattern is shown in FIG. 3b with the points labeled 5 being the places that are identically zero in the pattern corresponding to the local maxima of 3 in FIG. 3a.

Figure 5A:
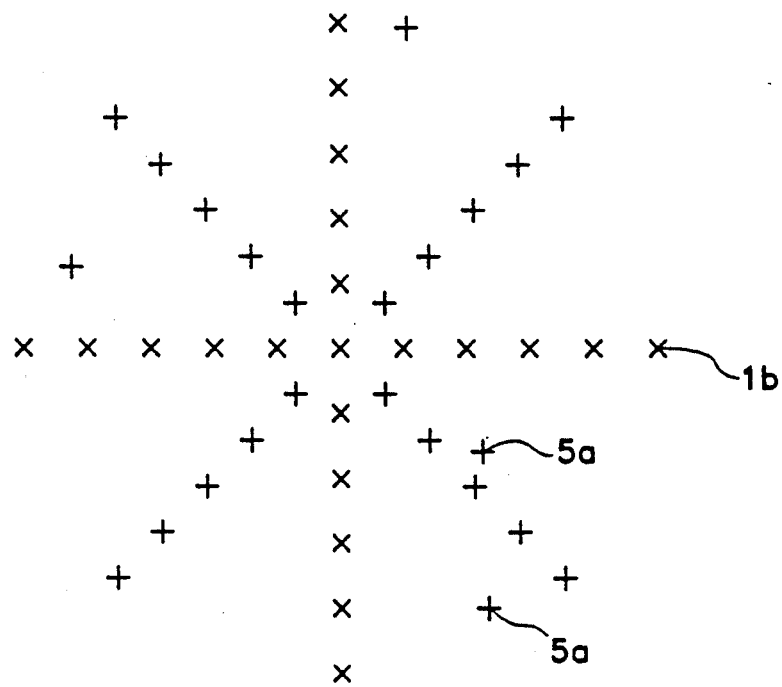
FIG. 5a shows the distribution of points found in FIG. 4. The points labeled 2 represent noise signals.
Figure 5B:
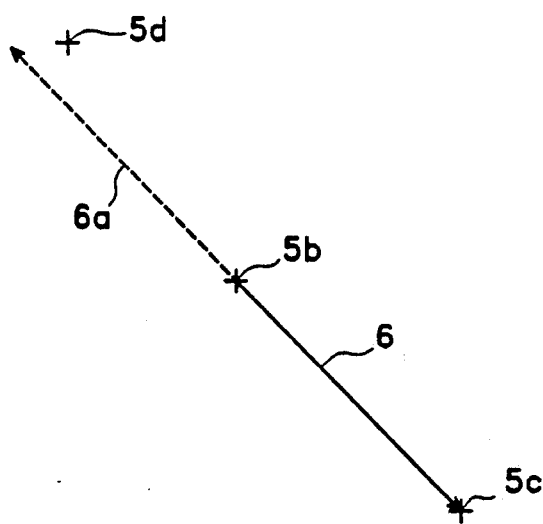
FIG. 5b illustrates the process of finding the point about which the pattern is symmetrical. A trial center point is denoted by 5b. The vector 5 denotes the vector from the trial center point 5b to a given test point 5c. The vector 6a depicts the reflection of vector 6 about the trial center 5b and the point 5d is a point near the reflected vector 6a, thus incrementing the score of point 5b.

The collection of points in $I_2$ that are zero must then be organized for subsequent analysis. These points are shown in FIG. 5a. Because of noise in the original input image, there are still a few noise spots in the pattern illustrated by 5a in this figure. These points are eliminated by the following procedure. The first step in the process is to find the center of the pattern represented by 107 in FIG. 8. The process assumes that each of the spots $I_2$ is the center of the pattern in turn and then examines the rest of the spots in the pattern to measure if they are symmetrical about the assumed center as illustrated in FIG. 5b. Point 5b denotes the assumed center. Point 5c is a test point. Vector 6 is the vector joining point 5c to point 5c. The operation of checking for symmetry involves reflecting the vector 6 about the point 5b and looking to see whether there is another point in the pattern near this reflection of the vector. In the case depicted, there is indeed a point nearby, namely point 5d, so the symmetry score for point 5b would be incremented. After using all the remaining points in the pattern as test points for the assumed center 5b, we would arrive at a total symmetry score for the assumed center 5b. After checking each point in the pattern as an assumed center, we arrive at a symmetry score for each point. The point with the highest symmetry score is the actual center of the pattern. While the process of finding the center of the pattern is a very simple operation for the human eye, even when points are missing and extraneous points find their way into the field of view, this is a nontrivial process for a computer. The process described as part of the present invention is robust even in the presence of noise.

Figure 6A:
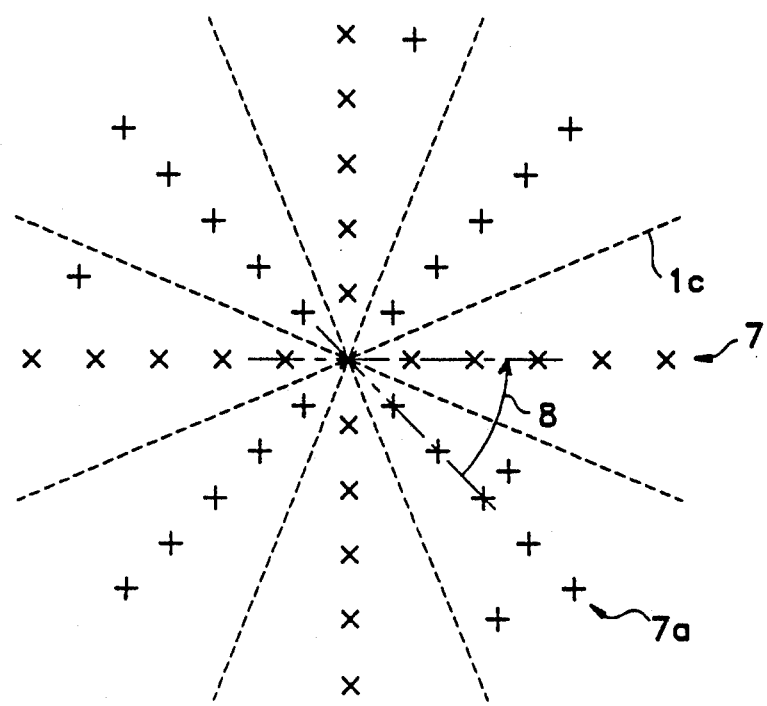
FIG. 6a shows the pattern of dots with angular bins as indicated in trace 1c. The horizontal axis is 7. To remove noise spots from one of the lines, say line 7a, the pattern 1c is rotated through angle 8 to give the result shown in FIG. 6b. The lines 9 show the discrimination threshold, in our case 5 pixels, and the points 5e represent points that are rejected since they lie sufficiently far off line.
Figure 6B:
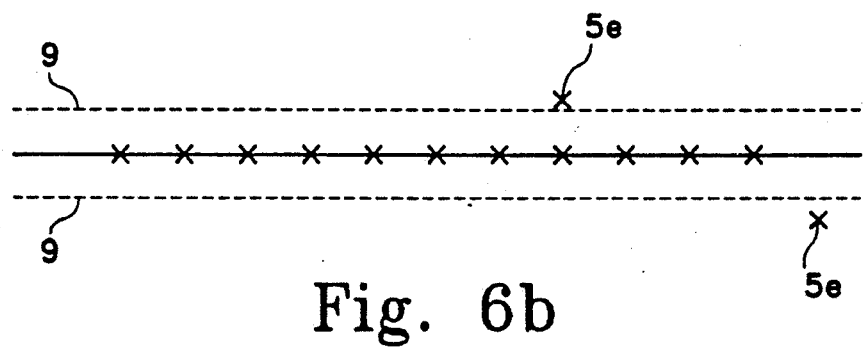

Once the center of the pattern has been identified, the angles of the pattern lines relative to the axis, known from the construction of the target, noted as 14 in FIG. 7, can be used to segregate the dots into distinct lines. This process is depicted in 108 of FIG. 8. FIG. 6a shows the pattern with segregated lines 1c drawn at the bisectors of the pattern lines. Any points that lie between adjacent segregation lines are considered to belong to the same line. The set of points 7 form the line that is on the horizontal axis of the system, while a line 7a corresponds to a line off the horizontal axis at an angle $\Omega$, shown as 8. Note that $\Omega$ is known from the fabrication of the target illuminator.

Each group of dots grouped as a line by process 108 of FIG. 8 is examined for extraneous dots. This is done in 109 of FIG. 8 by rotating each group through its corresponding angle $\Omega$ and deleting points that are more the discrimination value away from the horizontal axis. The discrimination levels 5 are used to keep points within the lines and delete points 6 which fall outside the criteria. This process is performed for each line in turn deleting points outside a given distance from the axis.

The final step in the process involves matching the detected points in the image with the known location of points in the illumination target 14 of FIG. 7. This process is represented by 110 in FIG. 8. Since the center point is known from process 107 of FIG. 8, it is the first point to be matched. Since the known angle of each of the target lines was used to get rid of noise pulses during the rotation of image lines, it can also be used to tell which group of dots goes with which line of the illumination target 14. While the magnification between the image and the target is unknown since it depends on the radius of curvature of the cornea, the average spacing of the dots on the illumination target line and the dots on the image line can be used to scale each line so that the two patterns are normalized. Thus the distances of the points on both the target and the image from the center are divided by their respective averages. The normalized points from both patterns are then examined to make sure that there is a corresponding point within a sufficiently small range chosen to be small compared to the normalized dot spacing. Any point in either the image or the target pattern that is found to be without a corresponding mate is discarded before the matched data set is sent to the profiling algorithm described by Sklar et al. (U.S. Pat. No. 5,054,907).

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. An ophthalmic diagnostic instrument for determining the shape of the cornea, comprising, an objective lens as an optical element of the instrument, on or symmetrically about an optical axis of the instrument, means for projecting a pattern of discrete separated point light sources and forming a real image of the pattern of point light sources at a position located between the interior of the objective lens and the eye, means for expanding the region of coverage on the cornea by using the objective lens as a field lens for the pattern image, means for selecting and collecting a reflected image of the pattern as reflected paraxially off the cornea, and for detecting a reflected position of substantially each point light source, as reflected from the cornea, including means for relaying the Fourier plane of the objective lens to a relayed position in the instrument, with aperture means positioned at said relayed position for limiting the collected light to that which is reflected paraxially off the cornea, whereby the aperture means is a spaced distance from the objective lens, means for analyzing the returned, collected pattern image and for filtering the noise from the pattern image using mathematical morphological transformations, means for comparing the filtered, collected pattern image to the undistorted pattern as projected, including analyzing the relative location and spatial orientation of the reflected point light sources as compared to the pattern as projected, and means for deriving mathematically a close approximation of a corneal surface shape that would give rise to such a collected pattern image.

2. Apparatus according to claim 1, wherein the pattern of discrete separated point light sources includes more than one rectilinear sequence.

3. Apparatus according to claim 1, wherein the pattern of discrete separated point light sources includes an asymmetrical shape having a plurality of lines of point light sources.

4. Apparatus according to claim 1, wherein the pattern of discrete separated point light sources lie along an invertible function of distance from the optical axis of the objective lens.

5. Apparatus according to claim 1, in combination with a surgical microscope having a standard auxiliary camera mount, and the ophthalmic diagnostic instrument being connected to the surgical microscope via the auxiliary camera mount, with an objective lens of the surgical microscope serving as the objective lens of the ophthalmic diagnostic instrument.

6. Apparatus according to claim 1, wherein the ophthalmic diagnostic instrument includes means for folding the pattern of discrete separated point light sources onto the optical axis of the instrument, toward the cornea, with the means for projecting the pattern including a source of the pattern off-axis from the optical axis and from the path of the returned, distorted pattern image.

7. Apparatus according to claim 1, further including means for projecting a variety of predetermined light patterns whose reflected image can be individually mapped isometrically onto a straight line simultaneously with said pattern of discrete separated point light sources, and means for separately analyzing distorted reflected light from the cornea relating to the invertible shapes and for providing separate, qualitative information which can be compared with the corneal surface shape derived via the pattern of discrete separated point light sources.

8. Apparatus according to claim 1, further including means for separately analyzing a secondary returned, reflected pattern image as reflected from the back or endothelial surface of the cornea.

9. Apparatus according to claim 1, further including means for separately analyzing a secondary returned, reflected pattern image as reflected from the anterior surface of the eye's lens.

10. Apparatus according to claim 1, further including means for separately analyzing a secondary returned, reflected pattern image as reflected from the posterior surface of the eye's lens.

11. Apparatus according to claim 1, further including means for separately analyzing a secondary returned, reflected pattern image as reflected from the retina.

12. Apparatus according to claim 1, further including means for separately analyzing a secondary returned, reflected pattern image as reflected from the floaters in the eye's vitreous.

13. Apparatus according to claim 8, wherein said means for separately analyzing includes filtering means for electronically separating returned light points on the detector means occurring from the front surface of the cornea from those occurring from the back surface of the cornea, by separating different ranges of amplitude of the detected light.

14. Apparatus according to claim 1, wherein the means for projecting a pattern includes an illuminating light source and a plate with a laser-cut or photolithographically produced pattern of discrete holes to form the discrete separated point light sources.

15. A method for determining the shape of the cornea of an eye, comprising, projecting a pattern of discrete separated point light sources and forming a real image of the pattern of point light sources at a position located in front of the eye, selecting and collecting a reflected image of the pattern as reflected paraxially off the cornea, and detecting a reflected position of substantially each point light source, as reflected from the cornea, analyzing the returned, collected pattern image, including filtering noise from the collected pattern image using mathematical morphological transformations, thresholding, or fast Fourier transformation techniques, comparing the filtered collected pattern image to the undistorted pattern as projected, including analyzing the relative location and spatial orientation of the reflected point light sources as compared to the pattern as projected, and deriving mathematically a close approximation of a corneal surface shape that would give rise to such a collected pattern image.

16. The method of claim 15, wherein the pattern of discrete separated point light sources comprises a generally asterisk shaped pattern with an intersection point at the optical axis of the instrument, and including means associated with the pattern for establishing a readily identifiable rotational orientation of the pattern.

17. The method of claim 15, wherein the pattern of discrete separated point light sources can be represented as any uniquely invertible function of position with respect to the optical axis of the image detection means.

* * * * *